(12) United States Patent
Coope

(10) Patent No.: US 6,426,065 B1
(45) Date of Patent: Jul. 30, 2002

(54) USE OF TRIS(HYDROXYMETHYL) AMINOMETHANE IN COLD PERMANENT WAVING PROCESSES

(75) Inventor: Janet Lynn Coope, Norwalk, CT (US)

(73) Assignee: Clairol Incorporated, Stamford, CT (US)

( * ) Notice: Subject to any disclaimer, the term of this patent is extended or adjusted under 35 U.S.C. 154(b) by 0 days.

(21) Appl. No.: 09/708,157

(22) Filed: Nov. 7, 2000

(51) Int. Cl.[7] .............................. A61K 7/09; A61K 7/06; C12Q 1/18
(52) U.S. Cl. ................... 424/70.5; 424/70.1; 424/70.2; 424/70.51; 435/32
(58) Field of Search .............................. 424/70.51, 70.1, 424/70.2, 70.5; 435/32

(56) References Cited

U.S. PATENT DOCUMENTS

| | | | | | |
|---|---|---|---|---|---|
| 5,520,909 A | * | 5/1996 | Salce et al. | ............... | 424/70.51 |
| 5,536,645 A | * | 7/1996 | Jay | ............... | 435/32 |
| 5,683,905 A | * | 11/1997 | Capon et al. | ............ | 435/320.1 |
| 5,853,706 A | * | 12/1998 | Klar | ............ | 424/70.1 |
| 5,935,795 A | * | 8/1999 | Lin et al. | ............ | 435/7.1 |

FOREIGN PATENT DOCUMENTS

| | | | | |
|---|---|---|---|---|
| EP | 0 129 807 | 1/1985 | ............ | A61K/7/09 |
| WO | 96/10986 | 4/1996 | ............ | A61K/7/09 |

* cited by examiner

*Primary Examiner*—Michael G. Hartley
*Assistant Examiner*—Michael A. Willis
(74) *Attorney, Agent, or Firm*—Charles J. Zeller

(57) ABSTRACT

There is provided a hair treatment composition for cold permanent hair waving. The composition has tris (hydroxymethyl)aminomethane and a reducing agent.

17 Claims, No Drawings

USE OF TRIS(HYDROXYMETHYL) AMINOMETHANE IN COLD PERMANENT WAVING PROCESSES

BACKGROUND OF THE INVENTION

1. Field of the Invention

The present invention relates to compositions used in permanent hair waving processes. More particularly, the present invention relates to hair treatment compositions that improve the styling and reshaping of hair using a cold permanent hair waving process.

2. Description of the Prior Art

Hair is made up of a fibrous protein called keratin. The shape and stability of the structure of this protein is provided by three interactions; (1) covalent bonding of cystine cross-linkages; (2) hydrogen bonding; and (3) salt linkages. The disulfide bonds in cystine are the strongest of these stabilizing forces.

To change the natural shape of hair, various treatments have been devised. One such treatment is permanent waving of hair, which can be used to either increase or decrease the amount of curl in hair. Permanent waving of hair may be performed using different types of treatments. One such treatment is heat waving, which facilitates the breakage of the disulfide bonds by applying heat in conjunction with alkali, or a combination of an alkali and a sulfite reducing agent. However, the heat treatment and chemicals involved tend to weaken the hair fibers and most of the reactions are irreversible. EP 129807 describes a heat waving process in which an amino acid free of a mercapto group is used in conjunction with an alkali, e.g., tris(hydroxymethyl)amino methane. According to EP '807 a reducing agent is not used in the disclosed heat waving process.

The heat waving method for permanent waving of hair has been replaced by the popular cold waving process, which restores the disulfide bonds as herein described. This technique for permanent waving uses chemical compounds that are capable of breaking the disulfide bonds and reshaping the hair without the provision of heat.

In cold waving, permanent waving is accomplished by a process that requires (a) chemically cleaving the disulfide bonds in hair with a reducing agent, (b) optionally rinsing the hair after cleaving the disulfide bonds, and (c) forming new disulfide bonds with an oxidizing agent while the hair is under tension in the new shape that is desired. The cold waving process is gentler to the hair than the heat waving process because the initial damage to the hair is largely reversible.

A lasting permanent wave can be achieved when the disulfide bonds are arranged in a new configuration. To reshape the hair, it is believed that 20% to 60% of the disulfide bonds must be broken and reconfigured in the new shape.

As stated previously, the reducing agent is used to break the disulfide bonds. Selection of a reducing agent is largely dependent upon the pH of the permanent cold waving composition. Generally, acidic cold permanent wave compositions employ reducing agents, such as glycerol mono-thioglycolate or bisulfates, and work in the lower pH range. On the other hand, cold alkaline permanent wave compositions utilize alkaline salts of thioglycolic acid. The reducing agent penetrates and swells the hair shaft thus enabling the disulfide bonds to be broken. In the cold waving process, a thiol compound, also known as a mercaptan, is typically used as the reducing agent.

Traditionally, ammonia and monoethanolamine have been used as alkalizers. However, there are drawbacks associated with these compounds. Ammonia performs well, but has a strong, irritating odor, which makes it unpleasant. Monoethanolamine has less of an odor and is commonly used as a substitute for ammonia. However, its pKa value is 9.50. This means that in a composition having a pH of 7.5, there is only one percent free amine. Thus, monoethanolamine is not as effective in such a composition. In the practice of cold waving, low heat is sometimes applied while the reducing agent is present on the hair. This accelerates the rate of cleaving of the disulfide bonds. When low heat is used, temperatures are generally less than about 50° C. during this step, usually below 30° C., but greater than room temperature.

One drawback to cold waving is the actual permanence of the change in shape of the hair. The newly configured hair tends to lose its shape when subject to normal stresses such as brushing, shampooing, and drying of the hair. These normal wear and tear stresses weaken the new disulfide bonds, which are constantly placed under tension.

Another drawback is the efficiency of the permanent wave. Efficiency has been characterized in the art as the tightness of the curl or "true to rod size." Although ammonia is effective at low pH, it has a strong harsh odor. Monoethanolamine can be used as a substitute, which has a more acceptable odor, but is less efficient at low pH.

SUMMARY OF THE INVENTION

It is an object of the present invention to provide a hair treatment composition that increases the longevity of a cold permanent wave.

It is another object of the present invention to provide such a hair treatment composition that increases the efficiency of a cold permanent wave.

It is also an object of the present invention to provide such a hair treatment composition that has a pH from about 6 to about 10.

It is another object of the present invention to provide a hair treatment composition that has a high percentage of free amine in the pH range of about 6.5 to about 9.5.

It is still another object of the present invention to provide such a hair treatment composition that exhibits a n acceptable odor.

These objects and advantages are achieved by the present invention, which is a hair treatment composition for cold permanent hair waving comprising tris(hydroxymethyl)aminomethane and a reducing agent.

DETAILED DESCRIPTION OF THE INVENTION

An essential component in the present hair treatment composition for cold permanent waving is tris(hydroxymethyl)amino methane ("Tris"), also known as tromethane. Tris serves as an alkalizer in the present composition. This compound has the structure shown in formula (I):

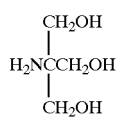

(I)

Tris is present in an amount from about 0.2 percentage by weight or weight percent (wt. %) to about 10 wt. % of the total weight of the present permanent waving composition. Cost considerations make levels above 10 wt. % undesirable. Preferably, Tris is present in an amount from about 0.5 wt. % to about 5 wt. % of the present composition.

The pKa of Tris is about 8.06. At a pH of about 7.5. Tris has about 22% free amine, which is significantly greater than monoethanolamine. In fact, monoethanolamine has only 1% free amine available at the same pH. This is a critical point because a higher percentage of free amine (a) increases the diffusion of the amine into the hair and provides a greater number of reactive sites for the reaction between the amine and the reducing agent, and (b) provides a better buffering system to hold the pH at the desired level.

The second essential component of the present hair treatment composition for cold permanent waving is a reducing agent. Any suitable reducing agent can be used. Such suitable reducing agents include, but are not limited to thiols (mercaptans), inorganic sulfides, sulfites, hydrosulfites, phosphines, cyanides, and combinations thereof. The preferred reducing agent is a thiol or sulfite compound.

In general, any suitable thiol compound that can be used in a permanent waving composition may be employed. Preferred thiols include, but are not limited to, glycerol monothioglycolate, cysteamine, thioglycolic acid and salts of thioglycolate acid, ammonium thioglycolate, monoethanolamine thioglycolate, cysteine thioglycolate, cysteine, thiolactic acid and its salts, iso-octyl thioglycolate, N-acetyl-L-cysteine, and combinations thereof.

The pKa of a particular reducing agent is important because it greatly affects the rate at which chemical equilibrium of the reducing reaction is reached. In the present composition, the pKa of the reducing agent is about 6 to about 10. Preferably, the pKa is about 6.5 to about 9.5, more preferably about 7 to about 9.

The reducing agent is present in the present composition in an amount from about 2 wt. % to about 30 wt. % of the total composition. Preferably, the reducing agent is about 5 wt. % to about 20 wt. % of the total weight of the permanent wave composition. More preferably, there is about 8 wt. % to about 15 wt. % of the reducing agent in the present composition. The actual amount of the reducing agent that is included is determined by the waving efficiency desired.

The present composition may also have other components or additives. The additives may include, for example, one or more swelling agents such as urea, diammonium dithiodiglycolate, other alkalizers, chelating agents, fragrances, dyes, opacifiers, pearlescing agents, thickeners, wetting and foaming agents, foam stabilizers, preservatives, softening agents, surfactants, acids, buffers, solvents, conditioners, and mixtures thereof.

Suitable materials for these purposes are identified in the International Cosmetic Ingredient Dictionary and Handbook (published by The Cosmetic, Toiletry and Fragrance Association)(Eighth Edition 2000). These materials may be included in the composition at concentrations effective to provide their intended function as commonly known in the art.

By including diammonium dithioglycolate in the permanent waving composition of the present invention, greater flexibility in processing time is gained, because it minimizes the possibility of overprocessing. That is, diammonium dithioglycolate forms an equilibrium reaction with the thiol reducing agent and with cysteine in the hair keratin, which proceeds to a certain point and thus minimizes the possibility of overprocessing the hair.

Examples of other alkalizers include, but are not limited to, ammonium hydroxide, ammonium carbonate, ammonium bicarbonate, ammonium chloride, monoethanolamine, and combinations thereof.

Chelating agents that bind metal ions in solution may be included in the present composition. Examples of these chelating agents are ethylene diamine tetraacetic acid (EDTA) and its derivatives such as tetrasodium EDTA, and 1-hydroxyethylene-(1,1 diphosphonic acid) sold under the tradename Dequest 2010® by Solutia.

Wetting and foaming agents can also be included in the composition to improve penetration of the composition into the hair thereby enhancing thiol diffusion. Examples include, but are not limited to conditioners such as quaternized fatty amines or silicones.

Opacifiers can be included in the composition to provide a milky appearance. Emulsions of acrylic, vinyl, and styrene polymers and copolymers are some examples of opacifiers that are suitable.

In a preferred embodiment, the hair treatment composition has an amount from about 0.2 wt. % to about 5 wt. % tris(hydroxymethyl)amino methane and from about 8 wt. % to about 15 wt. % of a thiol compound. The pH of this preferred composition is about 6.5 to about 9.5. Preferably, the pH is about 7.0 to about 8.5. More preferably, the pH is about 7.5 to about 8.0.

Optionally, tris(hydroxymethyl)amino methane may be combined with ammonia, monoethanolamine, or combinations thereof.

The present invention includes a cold permanent waving process comprising the steps of (a) applying to hair a permanent waving composition comprising tris (hydroxymethyl)amino methane and a reducing agent, (b) allowing the permanent waving composition to set for a sufficient time, (c) removing the permanent waving composition from the hair, and (d) applying a restoring agent selected from the group consisting of oxidizing agents, crosslinking agents, and mixtures thereof to the hair. Optionally, the cold waving process may further comprise step (e) shaping the hair, prior to step (a) or after steps (b) or (c). Preferably, removing step (c) is performed by rinsing with water. Optionally, low heat may be applied during step (b), e.g., heated air at a temperature generally less than 50° C., usually less than below 30° C.

In the cold permanent waving process, the permanent waving composition is typically applied as a lotion, cream, or gel, after the hair has been shampooed. The hair may be reconfigured into its new shape prior to or after applying the permanent waving composition. Next, the permanent waving composition is allowed to remain on the hair for a sufficient amount of time to break a sufficient number of disulfide bonds. This may require 1 minute to 60 minutes of contact time, typically from about 10 to about 30 minutes. Low heat, e.g., from a hood style dryer, may be applied if necessary and as described previously. The permanent wave composition is then removed from the hair. Generally, this entails thoroughly rinsing the hair with water. Then, the disulfide bonds are restored. This step is essential to increase the tensile strength of the hair. Oxidizing agents typically employed include, but are not limited to, hydrogen peroxide and bromates. Crosslinking agents that are suitable include, but are not limited to alkylene dihalides, dihalocarboxylic acids, dimaleimides, and the like.

To illustrate the present invention, the following examples are provided. However, it should be understood that the present invention is not limited to the examples described.

EXAMPLES

Three waving lotions were tested using aqueous solutions having 13.2 wt. % (0.8M) glyceryl monothioglycolate (GMT) and various concentrations of an amine alkalizer (ammonia, monoethanolamine, or Tris) as shown in Tables 1 and 2. The pH was adjusted using a 10 wt. % HCl solution. Tresses were rolled onto mandrels and evaluated using the permanent wave evaluation procedure that follows.

Procedure for Permanent Wave Evaluation

Each tress evaluation was conducted in quadruplicate to provide a measurement with a standard deviation of approximately 10%.

1. A bundle of 16 inch long medium virgin brown hair was secured with beeswax by dipping approximately 2 inches of the root end of the bundled hair into melted wax for 5 seconds. When the wax is cool to the touch, it is shaped into a square and allowed to harden.

2. Hair is broken into smaller bundles, washed with a 10 wt. % sodium lauryl sulfate solution and then rinsed.

3. Hair is sectioned into tresses of 45 hairs and the waxed end is re-waxed to further secure the tress. The wax is allowed to dry, and a piece of tape is wrapped around it to provide a writing surface. Tresses are trimmed to a length of 12 inches (30 cm) from the bottom edge of the tape.

4. An 8 cm long, 1.25 cm diameter spiral rod with 25 turns is used. The waxed end of the hair is secured between the $9^{th}$ and $10^{th}$ turns using a rubber band. The tress and rod are then soaked in a 0.1 wt. % solution of Triton X-100 (a mixture of octylphenoxypolyethoxyethanol and polyethylene glycol) for approximately 3 minutes.

5. A piece of tape, width 2.5 cm, is wrapped sideways around the bottom edge of the hair, covering the bottom 2.5 cm. A 3.4 g alligator clip is used to secure the tape. Using a piece of copper wire as a hook, a 6 oz. weight is hung from the tape at the bottom of the hair. The hair is rolled around the rod, using the weight to provide equal tension during rolling. The weight is removed after rolling, and the bottom tape is secured around the rod with a piece of Tygon tubing.

6. The rod is placed in a wide mouth test tube that contains 10 mL of the appropriate waving lotion, i.e. the composition of Examples 1, 2, 3 or 4. The solution completely covers the hair. The test tube is placed in a constant temperature water bath at 37° C. for 20 minutes.

7. The rod is removed and rinsed for 3 minutes under running tap water at approximately 30° C. and a flow rate of approximately 1 liter/minute. The rod is then placed into a new test tube with 10 mL of neutralizer (2 wt. % hydrogen peroxide, 0.05 wt. % polyquat-11, and phosphoric acid to pH 3.1). The rod is removed and rinsed with the 30° C. tap water for 2 minutes.

8. The tress is soaked in a bowl of 30° C. tap water for 5 minutes to allow complete oxidation. The tress is then carefully unrolled from the rod without tension, starting from the bottom and keeping the spiral configuration intact. The tape is cut off the hair using scissors while the hair is still on the rod.

9. The tress is hung by the top piece of tape and allowed to dry while hanging for 1 hour.

10. The tress is then hung in a glass container filled with a 0.1% Triton X-100 solution (by weight). A glass container (10×11.5×4 in) is used in which clear plastic rulers are glued along the front and back walls. A copper wire is secured across the top of the container. The rulers should be lined up to provide a way to accurately measure the hair. A copper wire hook is placed through the tape at the top of the tress and hung on the wire. The tress is soaked for 1 hour and then measured using the rulers in the water.

Waving Efficiency

After the procedure, the lengths of the tresses were measured in a water bath. The shorter the tress, the tighter the curl and the better the product.

The curl is measured from the end of the wax to the end of the curl.

$$\text{Wave efficiency} = \frac{L_i - L_t}{L_i - L_o} \times 100$$

where $L_i$=initial length of tress from wax end to tip $L_o$=length of tress when wrapped on the rod $L_t$=length of permed hair from wax end to tip, measured in the water Tables 1 and 2 show that Tris is an effective alkalizer for a low pH waving lotion.

TABLE 1

Use of Various Amines (0.75M) with GMT at pH 7.5

| Amine | Tress Length (cm) $L_t$ | Percent Waving Efficiency |
|---|---|---|
| Ammonia | 15.5 ± 1.2 | 47.8 |
| Monoethanolamine | 16.1 ± 0.5 | 45.4 |
| Tris | 15.7 ± 0.9 | 47.0 |

TABLE 2

Use of Various Amines with GMT at pH 8.0

| Amine | Molar Concentration of Amine | Tress Length (cm) $L_t$ | Percent Waving Efficiency |
|---|---|---|---|
| Ammonia | 0.4 | 14.5 ± 1.8 | 51.8 |
| Ammonia | 0.75 | 14.2 ± 0.6 | 53.0 |
| Monoethanolamine | 0.4 | 15.7 ± 1.9 | 47.0 |
| Monoethanolamine | 0.75 | 17.6 ± 1.1 | 39.4 |
| Tris | 0.2 | 16.2 ± 0.9 | 45.0 |
| Tris | 0.4 | 14.8 ± 0.9 | 50.6 |
| Tris | 0.6 | 16.9 ± 0.4 | 42.2 |
| Tris | 0.75 | 16.5 ± 1.4 | 43.8 |

CONCLUSIONS

Tris in combination with a reducing agent produces better results than monoethanolamine with a reducing agent.

Use of Tris is beneficial in the pH range of about 6 to about 10 using any thiol reducing agent. Better results are obtained at a pH of about 6.5 to about 9.5 and optimal results at a pH of about 7.5 to about 8.5. This invention is useful for preparing formulations without ammonia or in combination with ammonia, monoethanolamine, or mixtures thereof. Examples of thiols that are useful with this invention are glycerol monothioglycolate, cysteamine, thioglycolic acid, cysteine, dithiothreitol, dithioerythritol and thiolactic acid.

Having thus described the present invention with particular reference to preferred embodiments thereof, it will be apparent that various changes and modifications may be made therein without departing from the spirit and scope of the present invention as defined in the appended claims.

What is claimed is:

1. A cold permanent waving process for hair comprising the steps of:
   (a) applying to the hair a permanent waving composition comprising
      (i) from about 0.2 wt. % to about 10 wt. % tris (hydroxymethyl)amino methane,
      (ii) from about 2 wt. % to about 30 wt. % of a reducing agent selected from the group consisting of a sulfite compound and a thiol compound, and
      (iii) an additive selected from the group consisting of one or more of swelling agents, diammonium dithiodiglycolate, other alkalizers, chelating agents, fragrances, dyes, opacifiers, pearlescing agents, thickeners, wetting and foaming agents, foam stabilizers, preservatives, softening agents, acids, buffers, solvents, conditioners and mixtures thereof, wherein the pH of said composition is about 6.0 to about 9.5;
   (b) allowing said permanent waving composition to set for a sufficient time;
   (c) removing said permanent waving composition from the hair; and applying a restoring agent selected from the group consisting of oxidizing agents, crosslinking agents, and mixtures thereof to the hair.

2. The process of claim 1, wherein the reducing agent is a thiol compound present in an amount of from about 5 wt. % to about 15 wt. %, and is selected from the group consisting of glycerol monothioglycolate, cysteamine, thioglycolic acid and salts of thioglycolate acid, ammonium thioglycolate, monoethanolamine thioglycolate, cysteine thioglycolate, cysteine, thiolactic acid and salts of thiolactic acid, iso-octyl thioglycolate, N-acetyl-L-cysteine, and mixtures thereof.

3. The process of claim 1, wherein the composition contains an other alkalizer selected from the group consisting of ammonium hydroxide, ammonium carbonate, ammonium bicarbonate, ammonium chloride, monoethanolamine, and mixtures thereof.

4. The process of claim 1, further comprising the step of (e) shaping the hair, prior to step (a) or after steps (b) or (c).

5. The process of claim 1, wherein said removing step (c) is performed by rinsing the hair with water.

6. The process of claim 1 wherein the reducing agent is a thiol compound.

7. The process of claim 6, wherein said permanent waving composition has a pH of from 7.5 to 8.5.

8. The process of claim 7, wherein said thiol compound has a $pK_a$ of about 6 to about 10.

9. The process of claim 7, wherein said thiol compound is selected from the group consisting of glycerol monothioglycolate, cysteamine, thioglycolic acid and salts of thioglycolate acid, ammonium thioglycolate, monoethanolamine thioglycolate, cysteine thioglycolate, cysteine, thiolactic acid and salts of thiolactic acid, iso-octyl thioglycolate, N-acetyl-L-cysteine, and mixtures thereof.

10. The process of claim 1, further comprising the step (f) of applying low heat to the hair during step (b).

11. The process according to claim 1 wherein the permanent waving composition is a lotion in the form of an aqueous solution and has a pH of from 7 to 8.5 and the reducing agent is a thiol compound.

12. The process of claim 1, wherein said tris (hydroxymethyl)amino methane is present in an amount up to about 5 wt. % of the total weight of the composition.

13. The process of claim 7 wherein the permanent waving composition has a pH of from about 7.5 to about 8.0.

14. The process of claim 13, wherein said tris (hydroxymethyl)amino methane is present in an amount up to about 5 wt. % of the total weight of the composition.

15. The process of claim 14, wherein said reducing agent has a $pK_a$ of about 6 to about 10.

16. The process of claim 1, wherein said reducing agent is present in an amount up to about 15 wt. % of the total weight of the composition.

17. The process of claim 1, wherein component (iii) is diammonium dithiodiglycolate.

* * * * *